United States Patent [19]
Wirth et al.

[11] Patent Number: 6,023,799
[45] Date of Patent: Feb. 15, 2000

[54] ACTUATOR FOR A PATIENT SUPPORT TABLE

[75] Inventors: Robert Wirth, Hersbruck; Klaus Mueglich, Herzogenaurach, both of Germany

[73] Assignee: Siemens Aktiengesellschaft, Munich, Germany

[21] Appl. No.: 09/123,998

[22] Filed: Jul. 29, 1998

[30] Foreign Application Priority Data

Jul. 31, 1997 [DE] Germany .......................... 197 33 177

[51] Int. Cl.⁷ .................................................. A47B 13/00
[52] U.S. Cl. .................................. 5/601; 5/424; 378/209; 600/410; 600/425
[58] Field of Search ............................... 5/601, 600, 424, 5/611, 943; 600/410, 425; 378/209

[56] References Cited

U.S. PATENT DOCUMENTS

| | | |
|---|---|---|
| 4,589,642 | 5/1986 | Schnelle et al. |
| 4,972,852 | 11/1990 | Koob et al. .............................. 600/410 |
| 5,273,043 | 12/1993 | Ruike ...................................... 378/209 |

FOREIGN PATENT DOCUMENTS

| | | |
|---|---|---|
| PS 32 26 374 | 1/1991 | Germany . |
| PS 43 18 686 | 1/1996 | Germany . |

*Primary Examiner*—Alexander Grosz
*Attorney, Agent, or Firm*—Hill & Simpson

[57] ABSTRACT

An actuator for a patient support table, such as a table allocated to a magnetic resonance or computed tomography system, that is movable in vertical and horizontal direction, the motion mode being controlled with a control unit dependent on the actuation of the actuator, has two actuation positions enabling the movement mode to which two defined movement modes are respectively allocated. The currently allowable and implementable movement mode is dependent on the momentary table position.

5 Claims, 2 Drawing Sheets

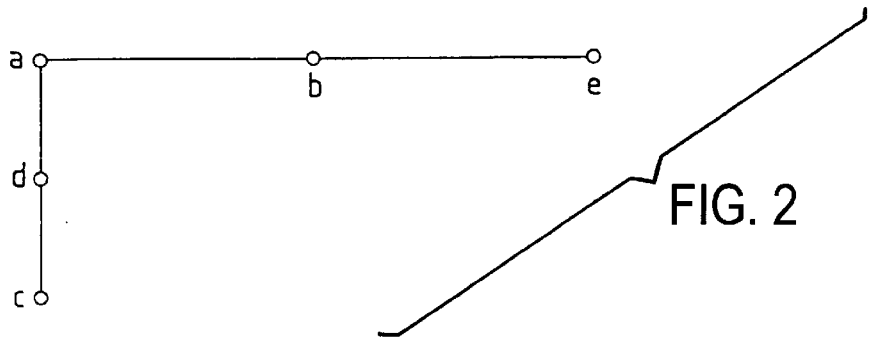
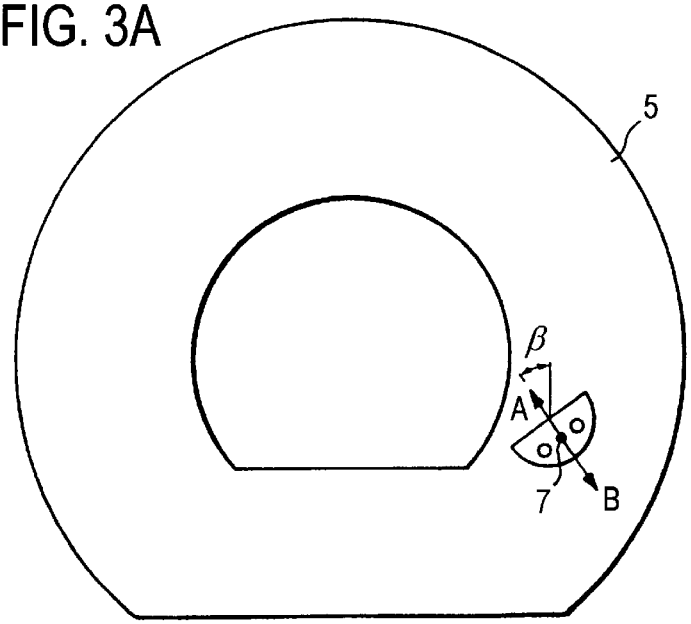
FIG. 2
FIG. 3A
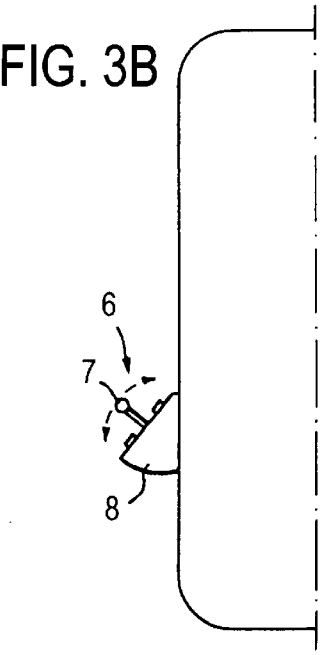
FIG. 3B

ACTUATOR FOR A PATIENT SUPPORT TABLE

BACKGROUND OF THE INVENTION

1. Field of the Invention

The present invention is directed to an actuator for a patient support table, particularly for a magnetic resonance or computed tomography system, that is movable in vertical and horizontal direction, whereby the motion mode is controlled by a control unit dependent on the actuation of the actuator.

2. Description of the Prior Art

An exactly controlled and coordinated motion mode is required for patient support tables that are allocated to magnetic resonance or computer tomography systems, since the patient support table in these systems is to be moved into and out of the examination tube by a horizontal motion and is also to be moved in a vertical direction for accepting or discharging the patient. The motion mode is controlled with a control unit allocated to the actuation mechanism. The operating event for a movement of the patient support table should ensue as simply and comfortably as possible, i.e. the necessity of making a number of manipulations and the like in order to enable a movement of the table should be avoided. Motion modes which are physically possible, but which should not be implemented in view of the current table position, should also be prevented in order to avoid collisions with the system or the like.

German PS 32 26 374 discloses a control device for an examination table that can be operated with a removable lever and a switch attached to the examination table.

German PS 43 18 686 discloses a method for the operation of a medical apparatus, wherein the patient table is moved into a standby position in emergency situations by actuating a single switch and an x-ray is moved to an end of a support plate.

SUMMARY OF THE INVENTION

An object of the present invention is to provide an actuator that offers a maximum of operating ease but also offers a high degree of movement dependability.

This object is achieved in accordance with the invention an actuator of the type initially described that having two actuation positions enabling the movement mode to which two defined movement modes are respectively allocated, with the currently allowable and implementable movement mode being dependent on the current table position.

In the inventive actuator, thus, a selection of that movement possibility that is allowed and implementable in view of the momentary table position is carried out by the control unit with particular advantage. To this end, defined movement modes are allocated to the respective actuation positions, such as a total of four movement modes, namely "raise", "lower", "enter", "exit", in an exemplary embodiment given vertical and horizontal movement possibilities. The operator thus needs to select only one actuation position in order to automatically select the correct movement mode. A selection in view of the allowability and implementability of the movement mode again ensues during the movement mode when an "extreme table position" is reached, and this is subsequently implemented as long as the respective actuation position is maintained for this movement mode. A maximum of operating ease is thus created, since only two actuation positions need to be selected, as is a maximum of motion dependability as well, since only defined movement modes corresponding to the actual momentary conditions are allowed.

As already stated, only four movement modes are possible in the exemplary embodiment. In a further version of this embodiment, a movement mode in a first vertical direction and a first horizontal direction is allocated to one actuation position and an opposite movement mode is allocated to the other actuation position. This means, for example, that the movement modes "raise" and "enter" are allocated to the first actuation position, and the movement modes "exit" and "lower" are allocated to the second actuation position. This division of the allowable and allocated movement modes is particularly advantageous in view of the use of the actuator for operating the patient support table in systems such as tomography systems.

The actuator can be in the form of a swivellable or pushable joystick, which is as simple as possible to operate. In order to further enhance the operating ease, the actuator can be built-in to a mount so that the movement direction proceeds at an angle of 45° in a plane normal to the joystick. This is advantageous that, for example, the actuator can be arranged at a separate operating console can likewise also be swivelled or pushed quasi obliquely up or down directly at the system itself. If the actuator positions that can be reached by a displacement obliquely up cause the movement modes "raise" and "enter", then this displacement coincides with the mental result of the intended movement mode on the part of the operator since the operator, of course, will preferably execute an upward motion for raising. The same, of course, applies with respect to the movement modes "exit" and "lower", whereby a downward motion should preferably ensue particularly for the latter.

Alternatively to the use of a joystick, the actuator can be formed by two key or touch elements, particularly press buttons. In this embodiment, the actuation positions are achieved by pressing the keys. The keys can be fashioned such that the allocated movement modes are automatically executed after pressing one of the keys, or the key for the execution of the respective modes must remain pressed for the time during which the movement should occur. The two key or touch elements, which can also be film keys or the like, are arranged opposite one another at an angle of 45° in the installation plane in their built-in position, possibly in a mount for the reasons described above.

In addition to the actuator itself, the invention is directed to a patient support table, particularly for magnetic resonance or computed tomography systems, having an actuator of the above-described type.

DESCRIPTION OF THE DRAWINGS

FIG. 2 is a tabular arrangement showing patient table positions, the allowed movement modes, as well as a graphic for explaining tabular arrangement.

FIG. 3A shows a plan view and FIG. 3B shows a side view of an inventive actuator in a second exemplary embodiment, arranged at a medical system.

DESCRIPTION OF THE PREFERRED EMBODIMENTS

Figure 1:
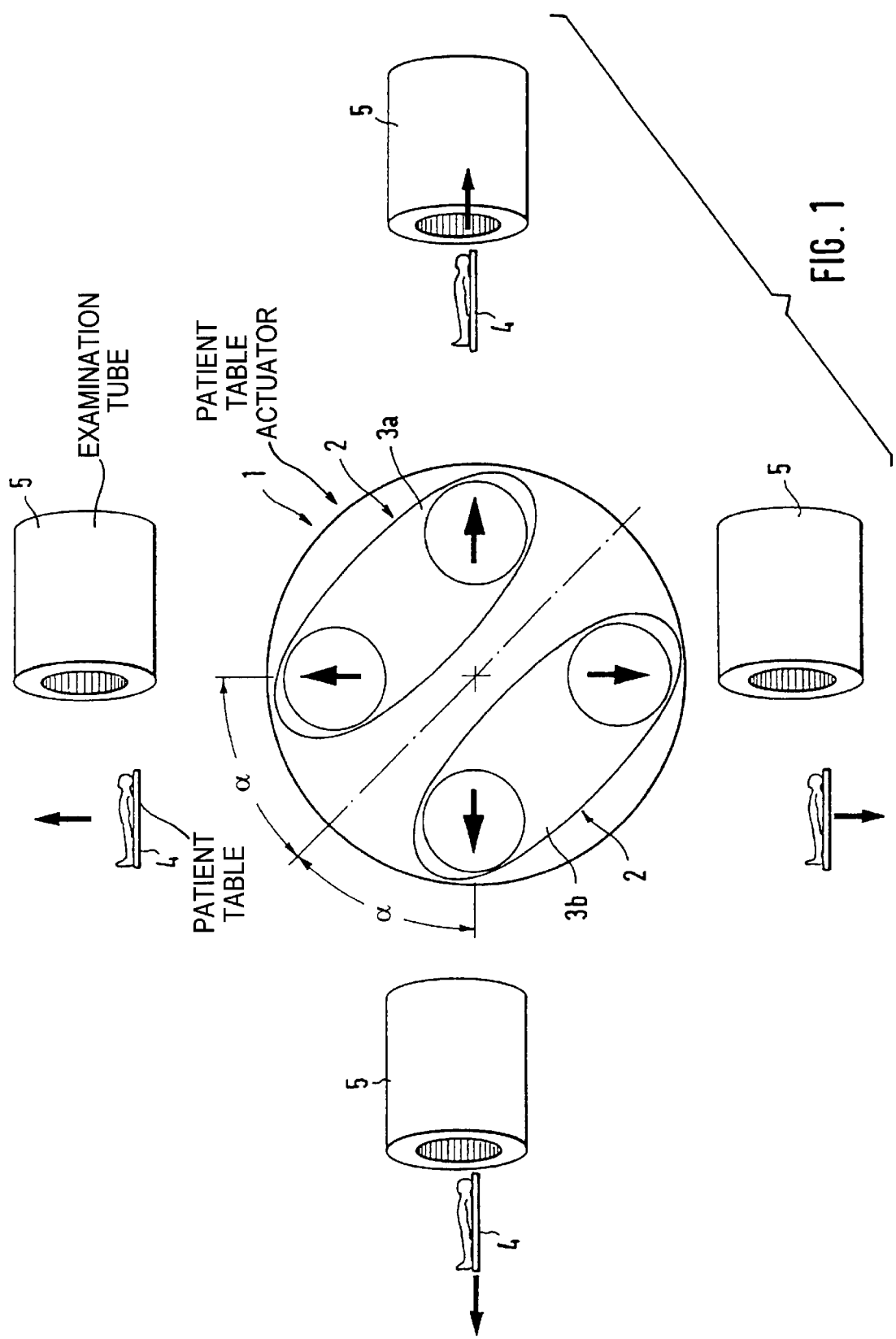
FIG. 1 is a schematic diagram explaining the various movement modes and their allocation to the actuator.

FIG. 1 is a schematic illustration of an actuator 1 and the allocated movement modes. The actuator 1 has two actuation elements 2 in the form of two key elements 3a, 3b, for example push buttons. The key elements 3a, 3b are arranged opposite one another and turned by an angle $\alpha=45°$, as shown with the circled arrows. Two possible movement modes are permanently allocated to each key elements 3a, 3b. The movement modes of "raise" and "enter" are allocated to the first key element 3a. "Raise" thereby denotes a vertical raising of the patient support table 4, as shown in the upper demonstration image. "Enter" denotes—see the allocated diagram at the right—a horizontal displacement of the patient support table 4 into the illustrated examination tube 5.

The movement modes of "exit" and "lower" are allocated to the key element 3b. "Exit", identified by the horizontal arrow pointing toward the left, denotes moving the patient support table 4 out of the examination tube 5 of, for example, a tomography apparatus. "Lower" denotes the lowering of the patient support table 4 from the raised position in order to change the patient (see the respective diagrams).

FIG. 2 shows a tabular arrangement with different table positions a, b, c, d and e and the different movement modes allowed for the current position of the patient table 4, symbolized by the respective arrows as also employed in FIG. 1. Further, the motion path of the patient support table 4, which can be moved along a vertical direction and an adjoining horizontal direction, is shown in a schematic diagram.

As can be derived from the tabular arrangement, a movement mode "lower" and "enter" is possible given a patient table position a. The patient table position a (see the movement curve) denotes that the patient support table 4 is raised but not introduced into the examination tube 5. In practice, this means that only the movement mode "enter" is selected as allowable given actuation of the key element 3a, to which the movement modes "raise" and "enter" are allocated, since a raising is no longer possible according to the momentary table position. When, by contrast, the key element 3b is actuated, to which the movement modes "exit" and "lower" are allocated, then the "lower" mode is selected as the only allowable and implementable movement mode since the table is already in the exited position.

When the table 4 is in the momentary position b, i.e. ultimately in a position between the raised, exited and the raised, entered limit position, then only "enter" or "exit" remain as allowed movement modes, i.e., upon actuation of the key element 3a, only the function "enter" is allowed and only the function "exit" upon actuation of the key element 3b. When the table 4 is then in the table position c, i.e. in the lowered position, then only the movement function "raise" is allowed and implementable, i.e. the key element 3a is to be actuated for a movement mode. A movement mode "enter" is precluded here and also cannot ensue since this would otherwise lead to a collision with the examination tube 5. The movement mode allocation shown in FIG. 1 assures this since the two competing movement modes are allocated to the same key element 3a, but only one thereof can be implemented.

If the table 4 is in a table position according to d, two opposite movement modes are again possible, namely the "raise" and "lower" functions, comparable to table position b. Finally, the table position e, wherein only the "exit" mode is allowable, is comparable to the table position c, i.e. operation only ensues given actuation of the key element 3b. No movement ensues when key element 3a is actuated.

As a result of the movement mode allocation according to FIG. 1, a movement mode, for example proceeding from table position c into table position e, can advantageously ensue merely by actuating the key element 3a, du to the corresponding allowability selection on the part of the control unit. During displacement along the vertical travel curve, namely, only the "raise" function according to key element 3a is allowable; when the position a is reached and the key element 3b continues to be pressed, a switch is automatically made to the occupied "enter" function, i.e. the control unit correspondingly controls the mode. The same is true of a reverse operation. The operating ease is thus considerably enhanced since only one key element has to be pressed. Collisions and the like are also precluded as a result of the inventive allocation.

FIGS. 3A and 3B schematically show another embodiment of an inventive actuator. This actuator 6 is fashioned as joystick 7 that can be swivelled around an axis. Here, the actuation device is arranged directly at the examination tube 5 at a control console 8. The joystick 7 is movable between two actuation positions. Corresponding movement modes are also permanently allocated to these actuation positions. This can be such that the movement modes "raise" and "enter" are allocated to the actuation position A and the movement modes "exit" and "lower " are allocated to the actuation position B. As FIGS. 3A and 3B reflect, the joystick 7 can be obliquely displaced at an angle $\beta$ of generally 45°. With respect to the movement mode dependent on the patient table position, the description set forth in this respect regarding FIG. 2 applies.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an apparatus having a patient support table which is movable in opposite vertical directions and in opposite horizontal directions, dependent on signals from a control unit, the improvement of an actuator for supplying signals to said control unit, said actuator having a first actuation position enabling a first movement mode, said first movement mode comprising a first vertical direction and a first horizontal direction, and a second actuation position enabling a second movement mode, said second movement mode comprising a second movement mode comprising a second vertical direction, opposite to said first vertical direction, and a second horizontal direction, opposite to said first horizontal direction, and means for actuating only an allowable and implemental movement mode dependent on a current position of said patient support table.

2. An actuator as claimed in claim 1 comprising a joystick.

3. An actuator as claimed in claim 2 wherein said joystick is disposed in a joystick plane, and further comprising a mount for said actuator having a plane normal to said joystick plane, said joystick being movable at an angle of approximately 45° in a plane normal to the joystick plane.

4. An actuator as claimed in claim 1 wherein said actuator comprises two depressable elements respectively allocated to said first movement mode and said second movement mode.

5. An actuator as claimed in claim 4 further comprising a mount for said depressable elements, having a mounting plane in which said depressable elements are disposed at an angle of 45° relative to each other.

* * * * *